(12) United States Patent
Widmann et al.

(10) Patent No.: US 9,782,413 B2
(45) Date of Patent: Oct. 10, 2017

(54) COMPOSITION FOR TREATMENT OF ESSENTIAL THROMBOCYTHEMIA

(71) Applicant: AOP ORPHAN PHARMACEUTICALS AG, Vienna (AT)

(72) Inventors: Rudolf Widmann, Purkersdorf (AT); Georg Strieder, Vienna (AT)

(73) Assignee: AOP ORPHAN PHARMACEUTICALS AC, Vienna (AT)

( * ) Notice: Subject to any disclaimer, the term of this patent is extended or adjusted under 35 U.S.C. 154(b) by 0 days.

(21) Appl. No.: 15/331,798

(22) Filed: Oct. 21, 2016

(65) Prior Publication Data

US 2017/0035768 A1 Feb. 9, 2017

Related U.S. Application Data

(63) Continuation of application No. 14/555,256, filed on Nov. 26, 2014, now abandoned, which is a continuation of application No. 13/637,014, filed as application No. PCT/EP2011/054628 on Mar. 25, 2011, now abandoned.

(30) Foreign Application Priority Data

Mar. 25, 2010 (EP) .................... 10157772

(51) Int. Cl.
| | |
|---|---|
| *A61K 31/519* | (2006.01) |
| *A61K 31/517* | (2006.01) |
| *A61K 47/12* | (2006.01) |
| *A61K 47/32* | (2006.01) |
| *A61K 9/20* | (2006.01) |
| *A61K 9/14* | (2006.01) |
| *A61P 7/00* | (2006.01) |
| *A61K 9/16* | (2006.01) |
| *A61K 47/38* | (2006.01) |

(52) U.S. Cl.
CPC .............. *A61K 31/519* (2013.01); *A61K 9/16* (2013.01); *A61K 9/20* (2013.01); *A61K 9/2013* (2013.01); *A61K 9/2027* (2013.01); *A61K 31/517* (2013.01); *A61K 47/12* (2013.01); *A61K 47/32* (2013.01); *A61K 47/38* (2013.01); *A61K 9/2054* (2013.01)

(58) Field of Classification Search
CPC .... A61K 31/519; A61K 47/12; A61K 31/517; A61K 47/32
See application file for complete search history.

(56) References Cited

U.S. PATENT DOCUMENTS

| | | | | |
|---|---|---|---|---|
| 7,993,654 | B2 * | 8/2011 | Woeller | A61K 8/0208 424/195.17 |
| 2008/0146581 | A1 * | 6/2008 | Barbera | A61K 9/4858 514/252.02 |
| 2009/0324710 | A1 * | 12/2009 | Glidden | A61K 9/4808 424/451 |
| 2010/0092552 | A1 * | 4/2010 | Jansen | A61K 9/2027 424/465 |
| 2013/0028945 | A1 * | 1/2013 | Widmann | A61K 9/2013 424/400 |

OTHER PUBLICATIONS

Chauvin, Tetrahedron Letters, 36: 397-400 (1995).*
Rey, "Uniformity of multiunit tablets under pilot plant conditions as a function of unit size and filler composition", University Dissertation-Tubingen (2003).*
Lubrizol, Carbopol Polymers for Controlled Release Matrix Tablets (2008), accessed at http://www.pharmtech.com/pharmtech/data/articlestandard/pharmtech/172009/595018/article.pdf on Sep. 6, 2013.*

* cited by examiner

*Primary Examiner* — Bethany Barham
*Assistant Examiner* — Lisbeth C Robinson
(74) *Attorney, Agent, or Firm* — Loza & Loza, LLP; Michael F. Fedrick

(57) ABSTRACT

The present invention relates to a novel pharmaceutical composition free of gastric coating comprising anagrelide hydrochloride in combination with a non-pH dependent polymer and a pharmaceutically acceptable water soluble acid and its use for the treatment of essential thrombocythemia.

9 Claims, 4 Drawing Sheets

COMPOSITION FOR TREATMENT OF ESSENTIAL THROMBOCYTHEMIA

CROSS-REFERENCE TO RELATED APPLICATIONS

Figure 1:
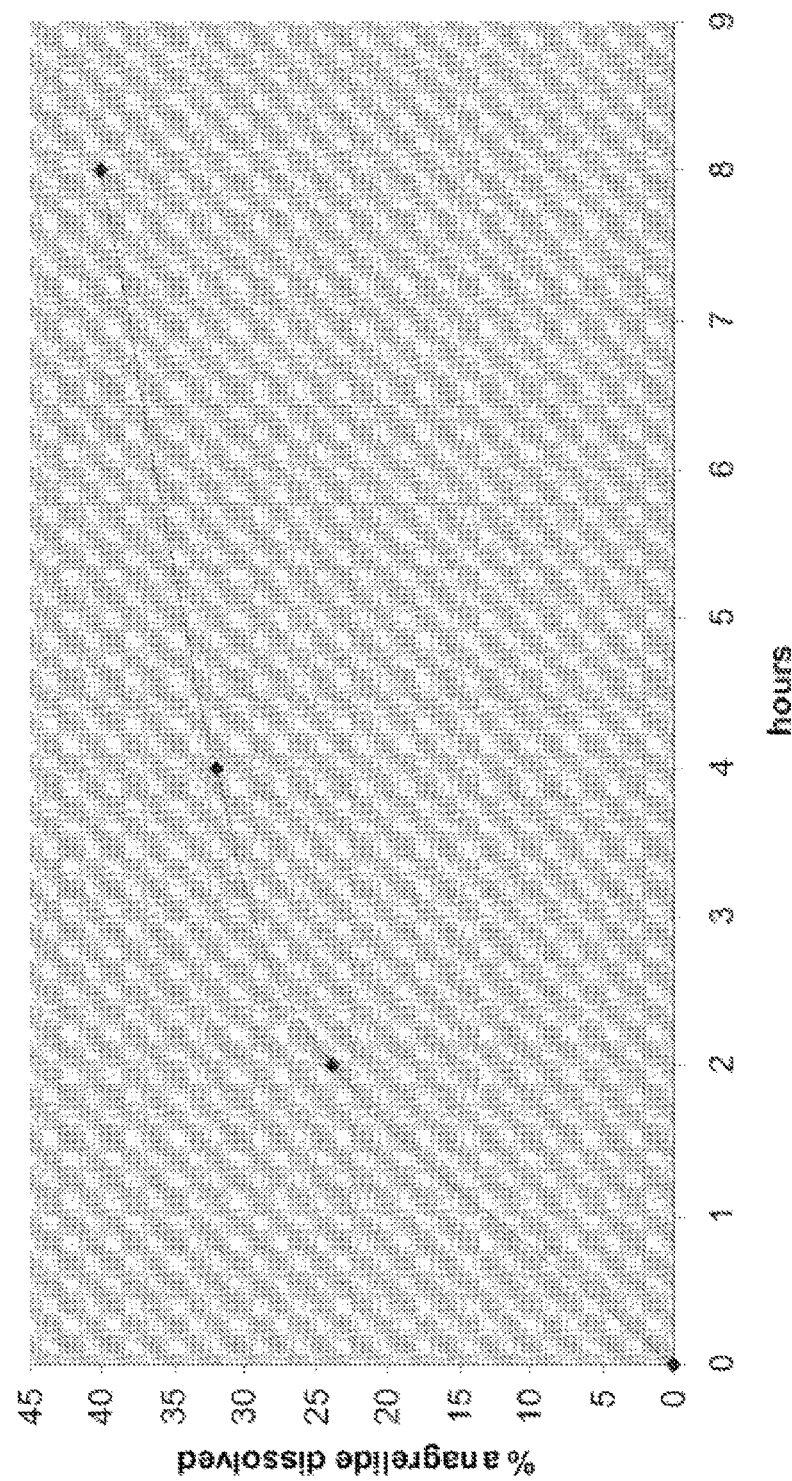

This application is a continuation-in-part which claims the benefit of priority under 35 U.S.C. 120 from U.S. patent application Ser. No. 14/555,256, filed on Nov. 26, 2014 and entitled NOVEL COMPOSITION FOR TREATMENT OF ESSENTIAL THROMBOCYTHEMIA, which is a continuation of U.S. patent application Ser. No. 13/637,014, filed on Sep. 24, 2012, which is the U.S. national stage of International Patent Application No. PCT/EP2011/054628, filed on Mar. 25, 2011, which claims the benefit of priority under 35 U.S.C. 119 from European Patent Application No. 10157772.4, filed on Mar. 25, 2010. The disclosures of the foregoing applications are incorporated herein by reference in their entirety.

FIELD OF THE INVENTION

The present invention relates to a novel pharmaceutical composition comprising anagrelide hydrochloride in combination with a non-pH dependent polymer and a pharmaceutically acceptable water soluble acid and its use for the treatment of essential thrombocythemia.

Primary thrombocythemia is a haematopoietic clonal or polyclonal myeloproliferative disease and is diagnosed in 12% of patients with thrombocytosis.

Essential thrombocythemia (ET) is the diagnosis in 45% of patients with primary thrombocytosis (1). In order to clearly differentiate ET from polycythaemia vera (PV) and myelofibrosis (MF), diagnostic criteria were defined by the Polycythaemia vera study group, (2) and later refined by the World Health Organization (WHO) diagnostic guidelines (3, 4).

The WHO diagnostic guidelines refined the PVSG diagnostic criteria for ET by the inclusion of bone marrow histopathology and argyrophilic (reticulin and collagen) fibre density to differentiate ET from early pre-fibrotic stages of idiopathic myelofibrosis (IMF) (5, 6, 7).

In patients with secondary thrombocytosis, platelet numbers above 1,500,000/µl represent an independent risk factor for thromboembolic and haemorrhagic events (8). Additional independent risk factors are a history of thromboembolism or bleeding, microvascular symptoms and age above 65 years (9, 10, 11, 12, 13). Clinical manifestations range from mild symptoms, such as headache, dizziness, and visual disturbances to life threatening complications such as thrombosis, haemorrhage and stroke. The estimated risk for thrombotic episodes is 6.6% per patient year, increases to 15% per patient year in patients over 60 years (14) and is highest in patients with previous history of occlusive episodes (10).

It is generally accepted that high-risk patients should receive platelet-lowering treatment. About 50% of patients show a history of thrombosis or haemorrhage at the time of diagnosis and fall into the high-risk category (15). Considering all independent risk factors such as platelet counts above 1,500,000/µl, age above 65 years and cardiovascular risk factors more than 50% of patients diagnosed with ET require treatment. In addition, symptomatic patients with platelet values below 900,000/µl are at risk for complications and require treatment (16). Large-vessel thrombosis may occur in young patients with platelet counts of less than 900,000/µl (17).

Reduction of platelet counts has been shown to reduce the risk for clinical complications (18). Platelet counts may therefore serve as a surrogate marker for clinical complications. Increasing evidence exists that young patients and patients with platelet counts less than 900,000/µl may benefit from treatment by reducing the risk of clinical complications and progressive vascular disease.

In recent years two treatment options were primarily pursued, hydroxyurea (HU) and Alpha-Interferon. However, hydroxyurea has disadvantages: 1. HU is not selective in lowering platelet numbers, and affects other blood components, 2. an increasing number of reports list severe side effects caused by HU, including leukemia. This is especially troublesome if young patients are treated for long periods of time. 3. Some patients are refractory to the treatment with HU.

Alpha-interferon requires subcutaneous administration, has multiple effects on other cell lineages and is not well tolerated by many individuals (19).

Anagrelide (Imidazo (2,1-b) quinazolin-2 (3H)-one,6,7-dichloro-1,5-dihydromonohydrochloride) is currently registered as a second line treatment option for patients with thrombocythemia. Its mechanism of action is selective for megakaryocytes and platelets. It can be administered orally. No evidence for long-term mutagenicity and leukemogenicity has been reported. Anagrelide has been licensed in the USA since 1997 and Europe since 2001. The currently approved therapeutic indication for Anagrelide in the EU is "for reduction of elevated platelet counts in at risk essential thrombocythemia patients who are intolerant to their current therapy or whose elevated platelet counts are not reduced to an acceptable level by their current therapy."

Anagrelide was originally developed as an inhibitor of platelet aggregation. Its mode of action involves inhibition of platelet cyclic AMP phosphodiesterase enzyme activity (20). However, this activity does not mediate platelet reduction. The selective platelet reducing activity is restricted to humans, occurs at much lower dose (21) and is mediated through inhibition of maturation of megakaryocytes (22, 23). Anagrelide does not affect megakaryocyte colony formation and platelet survival at therapeutic concentrations (22). The exact mechanism of action is currently unknown. However, metabolites of Anagrelide appear to have strong platelet lowering activity and therefore are likely to contribute to its action (24, 25, 26).

Current evidence and risk-benefit balance in the majority of patients favour Anagrelide as an appropriate treatment choice in a wider patient population. This also includes patients at risk younger than 60 years of age who are reluctant to start treatment with agents that pose a potential leukemogenic risk, such as hydroxyurea.

Anagrelide is extensively metabolized in vivo and more than five metabolites can be identified in urine by HPLC analysis (27). Two of these metabolites were identified, i.e. the biologically active 3-hydroxyanagrelide and the inactive 2-amino-5,6-dichloro-3,4-dihydroquinazolone (also called RL 603)(26).

Recent preclinical and clinical studies of pharmacologic aspects of anagrelide raise important questions regarding its mode of action and safety profile (26, 28, 29, 30, 31). It has been suggested that at least one already identified metabolite, namely 3-hydroxyanagrelide, contributes to the main pharmacological actions in vivo, which are platelet reduction and phosphodiesterase (PDE) 3 inhibitory activity, whereas RL 603 lacks these activities (24). Anagrelide is rapidly converted to 3-hydroxyanagrelide which reaches peak plasma levels about 45 mm later compared to the parent drug. It is highly likely that both compounds contribute to the pharmacological activity in vivo. Both anagrelide and 3-hydroxyanagrelide are rapidly eliminated from the blood, and there is no evidence for accumulation. It takes days to weeks until optimal platelet control is reached (29, 30). Therefore it is unlikely that platelet reduction is mediated by a direct pharmacologic activity. The molecular target mediating the long lasting platelet reducing effect on megakaryocytes is currently unknown, but may include modulation of c-MPL function resulting in altered thrombopoetin affinity (28). This hypothesis is supported by the finding that it takes 4 to 7 days after discontinuation of anagrelide for platelets to return to pre-therapy values.

In contrast, cAMP-dependent PDE 3 has been identified as the molecular target mediating acute effects of anagrelide on the cardiovascular system and on platelet aggregation (20). Headache, dizziness and palpitations represent frequent adverse events occurring in about 15 to 44% of patients during the first weeks of treatment and are probably mediated by mild cardiovascular and cerebral effects of anagrelide at therapeutic dose levels. The improvement of these side effects within 2 to 3 weeks is consistent with the development of tachyphylaxis (29), which also has been observed with other PDE 3 inhibitors (32). However, the rate and severity of cardiovascular side effects like hypotension increases with dose escalation above 5 mg, suggesting a correlation with plasma levels of anagrelide or, more importantly, 3-hydroxyanagrelide (29). Cases of reversible high output heart failure have been reported in patients treated with anagrelide (33, 34). A risk of heart failure after prolonged treatment was also observed in patients treated with milrinone, another positive inotropic PDE 3 inhibitor (35). However, 3-hydroxyanagrelide is considerably more potent than anagrelide as an inhibitor of PDE 3 (26). It may be hypothesized that 3-hydroxyanagrelide primarily mediates the cardiovascular side effects in patients treated with anagrelide. In particular, unpleasant cardiovascular adverse events such as palpitations, dizziness or headache may be caused primarily by 3-hydroxyanagrelide. These are troublesome for patients especially at the initiation of therapy and may be related to a reported discontinuation rate of up to 28% (29, 30).

When using different formulations of anagrelide, differences in adverse events have been reported, and the rate of patients discontinuing anagrelide was reported to range from 8 to 28% (29, 30, 31). Different pharmacokinetic properties can be correlated with pharmacodynamic differences with respect to tolerability and platelet reduction. A delayed absorption rate of anagrelide will be associated with reduced peak and overall plasma levels of anagrelide as well as significantly lower levels of 3-hydroxyanagrelide. As a consequence, a markedly lower rate of PDE 3-dependent acute side effects will be expected to occur.

U.S. Pat. No. 6,287,599 and US 2004/0062800 disclose pharmaceutical compositions with sustained release and reduced pH dependent dissolution profiles. Amongst others anagrelide containing tablets are described wherein 2.44 mg/tablet anagrelide HCl is contained, covered by Eudragit, a well known gastric coating.

WO2005/112917A1 describes compositions containing selective cytokine inhibitory drugs for the treatment of myeloproliferative diseases wherein anagrelide is present as second active agent.

US2007/104782A1 and WO2007/016350A2 describe pH independent release tablet formulations with enhanced mechanical properties containing a methacrylic acid copolymer.

US2005/0249814A1 and US2005/0008704A1 disclose formulations comprising a compound with at least one carboxylic acid moiety having rapid dissolution upon contact with physiological solvents.

US2004/0028729A1 describes a pharmaceutical preparation for modified release comprising a plurality of irregularly shaped non-spherical cores. Anagrelide is disclosed in combination with other additives together with Eudragit.

It is an object of the present invention to make available novel compositions of anagrelide with pH independent sustained release properties, which can be used for the prevention and treatment of symptoms related to chronic myeloproliferative disorders, such as essential thrombocythemia, but which lack some of the well known side effects of anagrelide treatment attributable to its main metabolite, 3-hydroxyanagrelide.

The object is achieved by the provision of the embodiments of the present application.

The invention relates to novel formulations of anagrelide resulting in a non immediate release of the active ingredient of anagrelide.

It has been shown that a pharmaceutical composition free of gastric coating comprising anagrelide HCl, a non-pH dependent polymer and a pharmaceutically acceptable water soluble acid have sustained and continuous release characteristics when administered to a patient.

Specifically, the anagrelide HCl is in the form of particles wherein at least 90% of said particles are smaller than 10 μm in diameter.

According to an embodiment of the invention, anagrelide HCl in an amount between 0.5 and 5 mg, preferably between 1 and 3.5 mg, preferably between 2 and 3 mg, preferably in an amount of about 2.3 mg. Specifically, anagrelide can have a mean particle size of about 5 μm.

According to a further embodiment, the non pH dependent polymer can be contained about 1.5 to 2.5 fold of the pharmaceutically active agent (w/w).

In the composition, the non-pH dependent polymer can be for example selected from the group of polyacrylacids, cellulose derivatives or polyacrylamids, preferably it is Carbopol™.

The polyacrylacid within the inventive composition can be comprised in an amount between 1 and 10 mg, preferably between 2.5 and 5 mg, preferably between 3 and 4 mg.

The inventive pharmaceutical composition can further comprise pharmaceutically acceptable water soluble acid which can be selected from, but is not limited to, the group of adipic acid, ascorbic acid, citric acid, fumaric acid, malic acid, succinic acid, tartaric acid or a mixture thereof, which, according to a specific embodiment, can be present in an amount between 5 and 40 mg, preferably between 10 and 20 mg, preferably between 15 and 19 mg.

Additionally, the inventive composition can comprise microcrystalline cellulose, specifically in an amount between 10 and 150 mg, preferably between 25 and 100 mg, preferably between 70 and 80 mg. Surprisingly, the composition was shown to have an in-vitro release of at least 45% after 8 hours without having any gastric coating.

In an alternative embodiment, a composition is provided containing anagrelide HCl, polyacrylacid, citric acid, microcrystalline cellulose and magnesium stearate. Preferably, the composition according is in the form of a tablet.

According to a further embodiment of the invention, the composition according can be used for the preparation of a medicament for the treatment of essential thrombocytemia.

FIGURES

FIG. 1: dissolution curve of anagrelide retard

Figure 2:
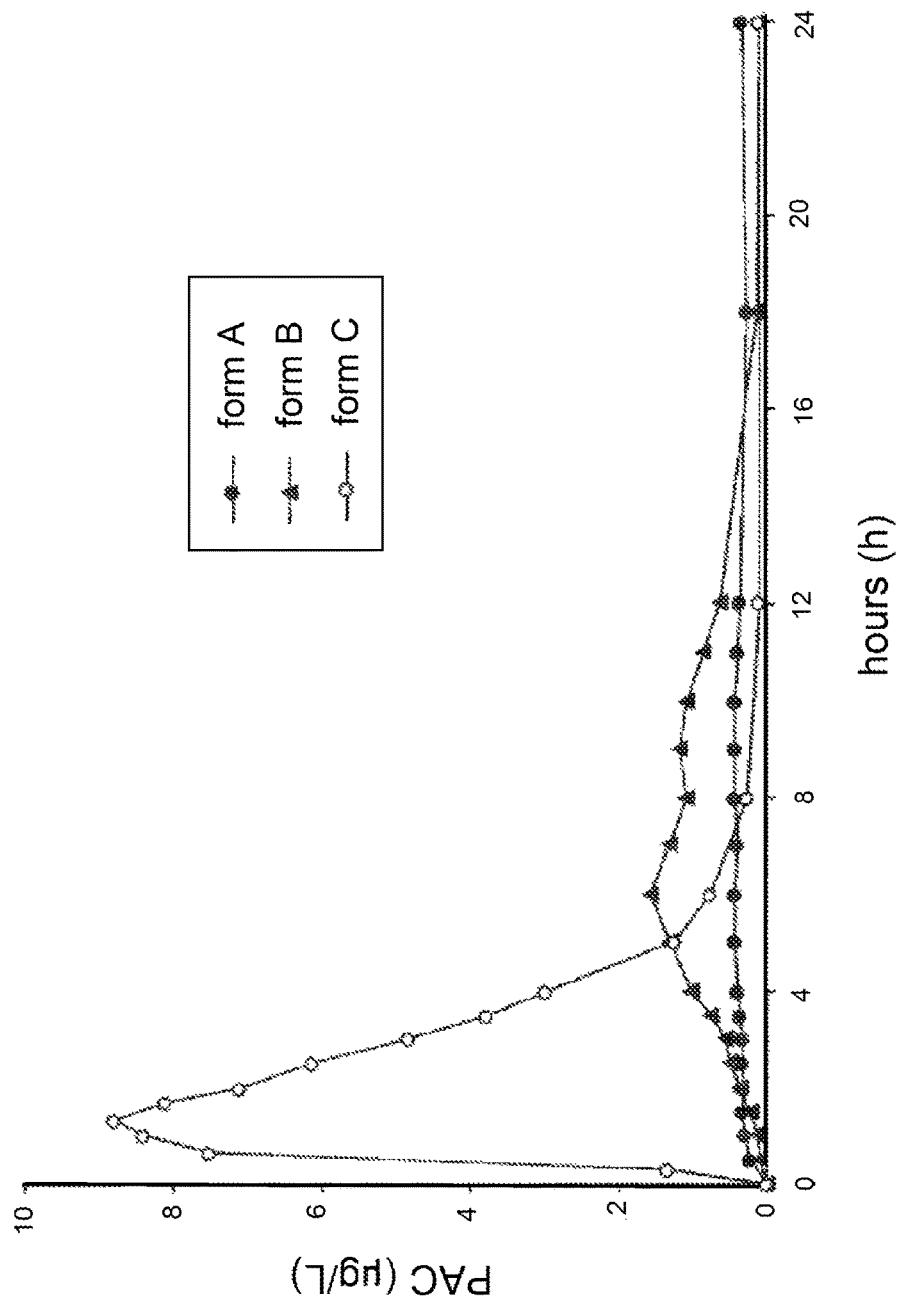

FIG. 2: typical plasma levels in comparison to immediate release formulation. Geometric means of plasma angrelide concentration—PAC (μg/L) versus time curves following a single oral 2 mg dose of anagrelide in 28 subjects.

Figure 3:
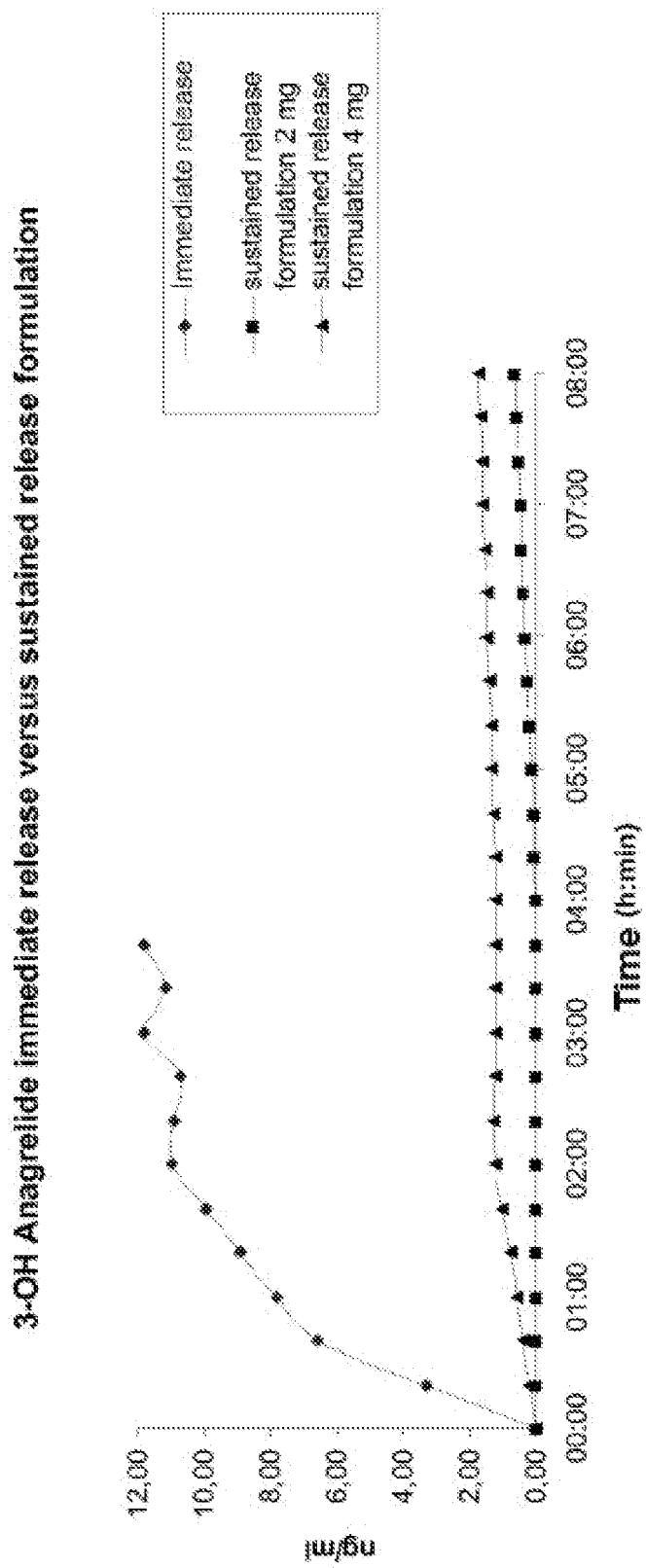

FIG. 3: 3OH anagrelide immediate release versus sustained release formulation.

Figure 4:
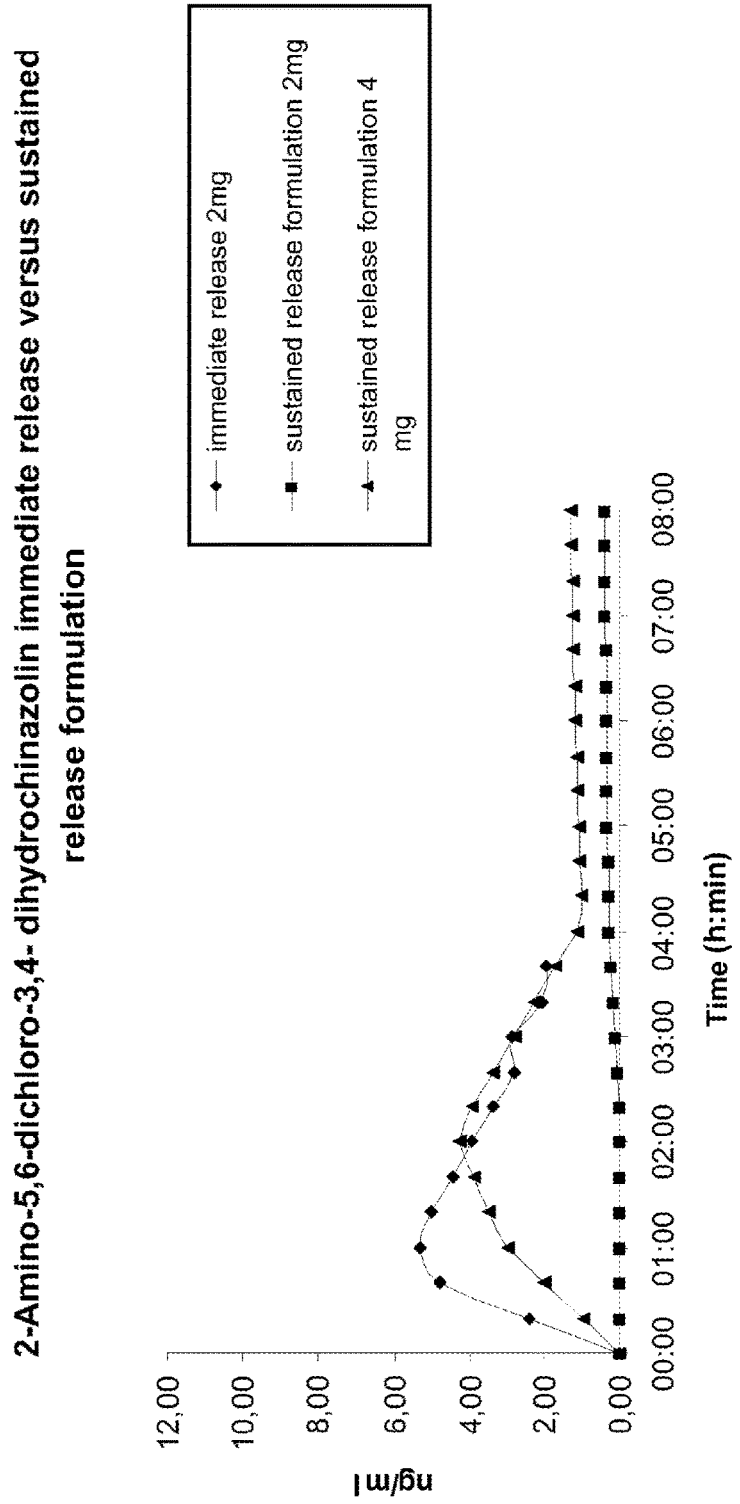

FIG. 4: 2 Amino 5,6-dichloro-3,4-dihydrochinazolin immediate release versus sustained release formulation

DETAILED DESCRIPTION OF THE INVENTION

The invention provides a pharmaceutical composition with sustained release properties free of gastric coating and comprising anagrelide hydrochloride in combination with a polymer which has pH independent swelling properties and a pharmaceutically acceptable and water soluble acid.

It was shown by the invention that although the administration form of the composition is not covered by any gastric coating, the pH dependent active agent anagrelide HCl is not immediately released but shows a non-immediate (retained release) release. The terms "sustained" and "non-immediate" release and "retained release" are used interchangeably in the present application.

The term "free of gastric coating" as used according to the present invention means that no coating is present on the surface of the composition that protects said composition from acids or acidic conditions as present in the gastric or enteric tract. Many active ingredients require a protective sealing coat which increases their stability and improves their mechanical properties. Examples of well known gastric coating agents are for example Eudragit™ which is a trade name for poly(methacrylic) acid, ethyl acrylate, sodium alginate, sodium carboxymethylcellulose.

Standard formulations of anagrelide HCl are gastric coated tablets or capsules to avoid rapid and complete dissolution in the gastric area which can lead to an unwanted increase of metabolites and can therefore result in unwanted side effects of the medicament.

It was surprisingly found by the inventors that the inventive preparation can avoid the presence of gastric coating on the surface of the tablets or capsules but still shows sustained dissolution due to its specific composition comprising a non-pH dependent polymer and pharmaceutically acceptable water soluble acid. Additionally, the inventive formulation shows a non-immediate but constant release of anagrelide not only in the gastroenteritic sections of highly acidic conditions but also release and adsorption of anagrelide in gastroenteritic sections of less acidic or neutral or basic conditions, for example at a pH higher than 5.5. The release of anagrelide HCl from the inventive composition is not pH dependent, i.e. it is performed not only at a pH≤4 and ≥9, but also at a pH between pH 4 and 9 thus providing solubility within the whole range of physiologic pH conditions of the gastrointestinal tract.

The terms "pH independent" or "non-pH dependent" polymer according to the embodiment mean that colloidal dispersion of said polymer is not pH dependent, i.e. is dispersed not only under high and low pH conditions, specifically at a pH≤4 and ≥9, but also between pH 4 and 9.

Any non pH dependent polymer known for the preparation of pharmaceutical compositions can be used for the invention. Specifically, the non pH dependent polymer according to the invention can be a polymer free of polyacrylacidic residues. Specifically, said polymers can be polyacrylacids, cellulose derivatives or polyacrylamids. More specifically the polymers are selected from the group of Polyacrylacid 971P (Carbopol™) or Hydroxyethylcellulose.

Non encapsulated polymers like for example Carbopol™ are preferred. Polymers and hydroxyethylcellulose swell when hydrated and form colloidal dispersions.

The ratio between anagrelide HCl and polymer is important due to its effect on the release properties of the composition. It is important to establish a weight ratio of polymer and agent wherein the release properties of anagrelide HCl are sustained but not completely inhibited. According to a specific embodiment of the invention the amount of the non pH dependent polymer is about 1.5 to 2.5 fold of the pharmaceutically active agent (w/w).

As an example, the inventors have shown that 10-fold excess of polymer compared to Anagrelide HCl, leads to strong inhibition of the Anagrelide release, thus leading to a release rate of Anagrelide of only approx. 30% after 16 hours.

Specifically, the non pH dependent polymer, specifically a polyacrylacid can be present in the composition in an amount between 1 and 10 mg, preferably between 2.5 and 5 mg, preferably between 3 and 4 mg.

According to a specific embodiment of the invention the amount of polyacrylacid is ≥1.5 and ≤2.5 fold with regard to the pharmaceutically active agent (w/w).

Due to the presence of water soluble acid in the pharmaceutical composition of the invention an acidic microenvironment within the formulation is maintained.

The pharmaceutically acceptable and water soluble acid can increase the dissolution rate and can for example be selected from the group of adipic acid, ascorbic acid, citric acid, fumaric acid, malic acid, succinic acid, tartaric acid or a mixture thereof. Preferably it is citric acid.

The water soluble acid can be present in an amount to maintain the acidic microenvironment within the preparation, for example it can be present in the composition in an amount between 5 and 40 mg, preferably between 10 and 20 mg, preferably between 15 and 19 mg.

Anagrelide is contained as anagrelide hydrochloride in an amount between 0.5 and 5 mg, preferably between 1 and 3.5 mg, preferably between 2 and 3 mg, preferably in an amount of about 2.3 mg.

The terms anagrelide, anagrelide particles and anagrelide HCl are terms used for the active compound Imidazo (2,1-b) quinazolin-2 (3H)-one,6,7-dichloro-1,5-dihydromonohydrochloride according to the present invention.

Anagrelide HCl according to the present invention can be present in the form of micronized anagrelide having a particle size of less than 15 μm, preferably less than 10 μm.

Preferably, the anagrelide hydrochloride of the inventive composition is present in the form of particles wherein at least 90% of said anagrelide particles are smaller than 10 μm in diameter.

The use of small particles of less than 15 μm, specifically less than 10 μm of anagrelide is specifically advantageous for pharmaceutical preparations as thereby a highly homogenous distribution and/or consistent release of the active ingredient anagrelide is provided when administered.

According to a specific embodiment of the invention the mean particle size of the anagrelide in the preparation is about 5 μm.

The term "mean particle size of about 5 μm" is defined according to the invention as at least 50% of the particles are smaller than 5 μm and at least 90% are smaller than 10 μm in diameter.

Micronization is known in the art as the process of reducing the average diameter of a solid material's particles. According to the invention "micronization" is performed by known techniques, for example by Rapid Expansion of Supercritical Solutions method, Supercritical Anti-Solvent method and Particles from Gas Saturated Solutions method.

Optionally, the inventive pharmaceutical composition may also contain bulking agents. Bulking agents include, but are not limited to microcrystalline cellulose, xylitol, mannitol, magnesium stearate, ethyl acetate, starches, lactose, sucrose, calcium sulphate, dextrose, sorbitol, cellulose powder, specifically in an amount between 0.01 and 5 mg, preferably between 0.1 and 2.5 mg, preferably between 0.25 and 1 mg Specifically, magnesium stearate can be present in the composition in an amount between 0.01 an 5 mg, preferably between 0.1 and 2.5 mg, preferably between 0.25 and 1 mg.

Disintegrating agents can also be contained in the inventive composition. Said agents include, but are not limited to microcrystalline cellulose, starches, sodium starch glycolate, crosscarmelose sodium, crospovidone.

Specifically, the composition contains microcrystalline cellulose. The microcrystalline cellulose can be contained in an amount between 10 and 150 mg, preferably in an amount between 25 and 100 mg, preferably in an amount between 70 and 80 mg.

The composition of the present invention can further include, but is not limited to other substances like antiadherants, glidants, lubricants and binding agents.

According to a specific embodiment of the invention the composition comprises anagrelide HCl, polyacrylacide, citric acid, microcrystalline cellulose and at least one bulking agent and optionally purified water.

Alternatively the composition can comprise anagrelide HCl, polyacrylacide, microcrystalline cellulose, purified water, water soluble acid selected from adipic acid, ascorbic acid, citric acid, fumaric acid, malic acid, succinic acid, tartaric acid or a mixture thereof and optionally magnesium stearate.

According to a specific embodiment the pharmaceutical composition comprises anagrelide HCl, polyacrylacide, citric acid, microcrystalline cellulose, purified water and magnesium stearate.

More specifically, the pharmaceutical composition comprises anagrelide HCl, polyacrylacide, citric acid, microcrystalline cellulose, purified water and magnesium stearate, wherein the anagrelide HCl is in the form of particles wherein at least 90% of said particles are smaller than 10 μm in diameter More specifically, a composition is provided wherein
anagrelide HCl is comprised in an amount between 0.5 and 5 mg, preferably between 1 and 3.5 mg, preferably between 2 and 3 mg, preferably in an amount of about 2.3 mg; wherein optionally wherein the anagrelide HCl is in the form of particles wherein at least 90% of said particles are smaller than 10 μm in diameter and polyacrylacide is present in an amount between 1 and 10 mg, preferably between 2.5 and 5 mg, preferably between 3 and 4 mg and provided that the amount of poylacrylacide is 1.5 to 2.5 fold of anagrelide, and citric acid is present in an amount between 5 and 40 mg, preferably between 10 and 20 mg, preferably between 15 and 19 mg and magnesium stearate is present in an amount between 0.01 an 5 mg, preferably between 0.1 and 2.5 mg, preferably between 0.25 and 1 mg and microcrystalline cellulose is present in an amount between 10 and 150 mg, preferably in an amount between 25 and 100 mg, preferably in an amount between 70 and 80 mg.

More specifically, the pharmaceutical composition comprises anagrelide HCl in an amount between 2 and 3 mg, polyacrylacide in an amount between 3 and 4 mg, citric acid in an amount between 15 and 19 mg, microcrystalline cellulose in an amount between 70 and 80 mg, purified water and magnesium stearate in an amount between 0.25 and 1 mg.

It has been shown that the inventive composition shows advantageous characteristics in view of sustained and constant release properties of the active agent. Anagrelide HCl containing compositions as presently used are immediate release medicaments wherein more than 90% of anagrelide is released in vitro within the first ten minutes. The novel formulation of anagrelide, in contrast, releases only app. 14-20% of anagrelide during the first hour in vitro, and it takes up to 16 hours for release of up to approx. 90% in vitro.

According to the present invention the terms "non-immediate" or "sustained" release mean that it takes at least 15 minutes until about 85% of the active agent is released or dissolved The dissolution rate is performed according to the European pharmacopeia monograph 2.9.3.

Dissolution test for solid dosage forms, chapter "Delayed release solid dosage forms", method A. The dissolution rate is defined according to table 2.9.3.2 of the same monograph with:

0.1 M HCl:
15-35% after 2 h
Level $L_1$, $L_2$ or $L_3$ must comply
Phosphate Buffer, pH 6.8:
30-50% after 8 h (total time)
Level $L_1$, $L_2$ or $L_3$ must comply Specifically, the pharmaceutical composition according to the invention gives rise to plasma peak concentrations of at least 0.2 μg/l, preferably at least 0.5 μg/l, preferably at least 0.75 μg/l after 6 hours under fasting conditions and plasma peak concentrations of 0.75 μg/l, preferably 1.5 μg/l, preferably 2.43 μg/l under fed conditions upon oral administration in vivo.

The inventive composition can be administered orally, for example in the form of tablets or capsules. According to the present embodiment, tablets are a specific pharmaceutical form for oral administration.

Specifically in view of better tolerability and reduction of negative side effects as well as the needs of long term treatment it is preferred to have a medicament that is of sustained release resulting in a delayed but more constant supply with anagrelide. Specifically, when using the inventive pharmaceutical composition, anagrelide can be measured in the plasma as plasma peak approximately after 30 minutes, preferably after 4 hours, more preferably after 6 hours after the composition is administered to the patient.

More specifically, the composition according to the invention has sustained in-vitro release of at least 45% after 8 hours.

Specifically in view of a better tolerability and reduction of negative side effects attributable to 3-hydroxyanagrelide it is preferred to have a medicament that is of sustained release resulting in a delayed supply with anagrelide and hence lower peak plasma levels of 3-hydroxyanagrelide. A reduction of 3-hydroxyanagrelide plasma peak levels of at least 2.5%, preferably of at least 5%, more preferred of at least 10% compared to immediate release anagrelide formulations can be provided by the inventive composition.

The anagrelide HCl containing composition according to the invention further shows improved tolerability due to the fact that the plasma concentration of anagrelide HCl is low due to the sustained release characteristics of the inventive medicament which avoids unwanted accumulation of the metabolite 3-hydroxyanagrelide.

Due to the novel release properties of the inventive compositoeis it is specifically useful for the first line treatment of essential thrombocythemia but can be used for second line treatment as well. The inventive composition is preferred specifically in the treatment of newly diagnosed patients, since unpleasant cardiovascular adverse events such as palpitations, dizziness or headache usually occur during the first weeks of treatment and may lead to early discontinuation of anagrelide therapy or decreased patient compliance.

Alternatively, the inventive composition can also be administered to patients who are intolerant to their current therapy or whose elevated platelet counts are not reduced to an acceptable level by their current therapy.

The recommended starting dose is 2 mg/d for 1 week, and the dose is weekly adjusted until optimal platelet control is achieved. Usually a reduction of platelet counts is achieved at a dose of 1 to 3 mg/d.

The desired dose of anagrelide HCl may conveniently be presented in a single dose or as divided dose at appropriate time intervals. Specifically, the anagrelide HCl containing composition may be administered several times throughout the day until the dose to get reduction of platelet counts is achieved, specifically it is administered in the morning and in the evening. Essential for the new formulation is the administering of the dose under "fed conditions" (after breakfast or dinner) as the rate of resorption is increased after food intake.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

In Vitro Dissolution Study:

The analysis was performed according to the European Pharmacopoeia (method 2.9.3, (36)) "dissolution test for solid dosage forms" via the paddle method, which requires that the solid dosage form is placed into the apparatus containing an appropriate medium (500 ml) at 37+/−0.5° C. and a defined operating rate for the paddle.

The anagrelide HCl formulation was composed as follows:
  2.2 mg anagrelide HCl
  polyacrylacide
  citric acid
  microcrystalline cellulose
  purified water
  magnesium stearate.

Dissolution Conditions:
  Instrument: Sotax AT7 smart or equivalent instrument
  Temperature: 37° C.±0.5° C.
  Apparatus: Paddle 75 rpm
  Medium: 750 ml HCl 0.1 mol/l; buffer adjustment to phase 2 after 2 hours
  Filter: Whatman GF/D (2.7 μm glass fibre or equivalent)
  Sampling: Sample are taken after 2 h, 4 h and 8 h (fraction collector 1 ml sample volume, removed volume is replaced)

Dissolution Procedure:

Phase 1 (HCl 0.1 mol/l):

Transfer 750 ml HCl 0.1 mol/l into every of the dissolution flask and heat to 37° C.±0.5° C. One Anagrelide tablet is added and the dissolution is started at 75 rpm. Samples (1 ml) are taken automatically from each flask after 2 hours and the removed volume is replaced by 1 ml HCl 0.1 mol/l.

Phase 2 (Buffer Adjustment to pH 6.8):

After the 2 hours sampling the buffer is adjusted. Therefore, 200 ml of sodium phosphate 0.25 mol/l tempered to 37° C. and 50 ml of sodium dodecyl sulphate are added to every dissolution flask. The pH is adjusted to pH 6.8±0.05 with HCl 2 mol/l or NaOH 2 mol/l. The dissolution testing is not interrupted by this procedure. Samples (1 ml) are taken automatically from each flask after 4 and 8 hours after start of phase 1 and the removed volume is replaced by 1 ml HCl 0.1 mol/l.

HPLC Conditions for Dissolution:
  HPLC-column: MZ LiChrospher-60-RP-Select-B-5 μm, 250×4.6 mm
  Detector wavelength: 254 nm (16); Ref 450 nm (80)
  Flow rate: 1.75 ml/min
  Column temperature: 30° C.
  Sample temperature: 20° C.
  Injection volume: 20 μl
  Mobile phases: 30% acetonitrile: 70% phosphate buffer pH 3.0 (isocratic)

The results are shown in FIG. 1. Constant dissolution of the anagrelid formulation according to the invention is shown at a pH 6.8.

Example 2: Pharmacokinetic Study

A pharmacokinetic study was performed to compare the bioavailability of present (C) and novel formulation (A, B) of anagrelide in a two period single dose, double-blind cross over study (wash out period 7 days) at a dose of 2 mg (orally given as one dose). Volunteers were 28 healthy males and females fasted with inclusion and exclusion criteria as recommended by respective guidelines (37). A clinical and laboratory screening was conducted, vital signs taken and a physical examination performed. The estimated sample size of at least 28 subjects gave a power of >0.8 at a CV<0.235 for the bioequivalence interval of 80-120%. A randomisation code was generated by the biostatistician according to which the volunteers were assigned to treatment novel and present formulation, in random order. Treatment compliance was assured by quality assured procedures, Time points for collection of blood for treatment A (treatment with the sustained release anagrelide HCL composition according to the invention under fasting conditions); B (treatment with the sustained release anagrelide HCL composition according to the invention under fed conditions) were before dosing (at 0 hr), and 0.5 hr, 1 hr, 1 hr 20, 1.5 hr, 2.0 hr, 2.5 hr, 3.5, 4.0 hr, 4.50 hr, 5.0 hr, 6.0 hr, 7.0 hr, 8.0 hr, 9.0 hr, 10.0 hr, 11.0 hr, 12.0 hr, 18.0 hr and 24 hr after administration of the drug.

For treatment C (immediate release anagrelide composition according to the state of the art) the blood sampling frequency was: 0.33 hr, 0.67 hr, 1.0 hr, 1.33 hr, 1.67 hr, 2.0 hr, 2.5 hr, 3.0 hr, 3.5 hr, 4.0 hr, 5.0 hr, 6.0 hr, 8.0 hr, 12.0 hr and 24 hr after administration of the drug. Blood samples were immediately centrifuged for 10 mm at 3000 rpm at +4° C. Adverse events were recorded by clinical research personal blinded to treatment. The statistical plan defined that all primary parameters i.e. the pharmacokinetic parameters were to be presented with a 90% CI, and for all additional parameters descriptive statistics was used. Pharmacokinetic parameters (AUC0-∞, Cmax, tmax, and t½) were calculated with Kinetica 2000® Version 4.2 (Innaphase Clinical Information Engineering, Philadelphia, Pa., USA). Statistical analysis for bioequivalence of the two formulations was performed by Analyses of Variance (ANOVA) on values of target parameters in order to estimate residual error and thus to construct confidence intervals including evaluation of the presence of period or sequence effects. The following programs were used: for the statistical analysis SAS® Version 8.1 (SAS® Institute, Cary, N.C., USA), for the test of normality distribution of calculated pharmacokinetic parameter data SAS® PROC INSIGHT (Distribution Test), for ANOVA calculations of the pharmacokinetic parameter data SAS® PROC GLM (General Linear Models) or PROC MIXED (Mixed Models) and for the non-parametric analyses of tmax the EQUIV-Test® (Statistical Solutions, Broadway, Mass., USA). Bioequivalence was assessed according to current guidelines with predetermined limits of 80 to 125% for the CIs of Test/Reference dugs for Cmax and AUC0-∞ at a power of 80% (37). The number of total adverse events was analysed by a paired Student's T test. (Table 1).

| Symptom | Incidence after A | Incidence after B | Incidence after C | Total Incidence |
|---|---|---|---|---|
| Headache | 4 | 8 | 9 | 21 |
| Dizziness | 1 | 3 | 5 | 9 |
| Palpitations | 0 | 1 | 8 | 9 |
| Vomiting | 0 | 0 | 1 | 1 |
| Extrasystoles | 0 | 0 | 1 | 1 |
| ALT elevation | 0 | 1 | 0 | 1 |
| Tachycardia | 0 | 0 | 1 | 1 |
| ALT, AST and bilirubin elevation | 0 | 0 | 1 | 1 |
| Chills | 0 | 0 | 1 | 1 |
| Hematoma | 1 | 0 | 0 | 1 |
| Total | 6 | 13 | 27 | 46 |

There is apparent trend towards rising total incidences of adverse events in the rank of treatments A, B, C, which can be also seen in most frequent adverse events known with anagrelide like headache and palpitations.

When anagrelide plasma levels were compared in 24 volunteers after the ingestion of novel or present anagrelide formulations, different profiles for both drug formulations became evident.

The results of the plasma levels of the lead compound anagrelide also strongly correlate with its major two metabolites 3-OH-anagrelide and 2-amino-5,6 dichloro-3,4 dihydrochinazolin. The plasma levels after treatment A and B (fasting and fed conditions for the sustained release formulation) of 3-OH-anagrelide show considerable lower levels with Cmax for 3-OH anagrelide of 1.71 µg/L respectively 5.26 µg/L compared with treatment C with immediate release formulation with mean Cmax 18.89 µg/L. Similar results were received with regards to 2-amino-5,6-dichloro-3,4-dihydrochinazoline with levels of 0.80 µg/L respectively 1.90 for the sustained release formulation and 4.3 µg/L. In addition also the food effect of the metabolite levels is significantly present at the retard formulation. Since for the sustained release formulation there is apparently no accumulation of metabolites which are primarily responsible for the adverse effects of the drug. This effect on the plasma levels of the main metabolites of anagrelide has already been demonstrated in preformulation studies and comparison of the sustained release formulation with the immediate release form. A representative overview of the difference in plasma levels of metabolites between immediate and sustained release formulation is demonstrated in FIGS. 3 and 4.

Typical plasma levels in comparison to immediate release formulation is shown in FIG. 2

Form A: sustained release formulation (fasted conditions), Form B: sustained release formulation (fed conditions), form C: immediate release formulation

REFERENCES

1. GRIESSHAMMER, M., BANGERTER, M., SAUER, T., WENNAUER, R., BERGMANN, L., HEIMPEL, H. (1999). Aetiology and clinical significance of thrombocytosis: analysis of 732 patients with an elevated platelet count. Journal of Internal Medicine 245, 295-300

2. MURPHY, S., PETERSON, P., ILAND, H., LASZLO, J. (1997). Experience of the Polycythemia Vera Study Group with essential thrombocythemia: a final report on diagnostic criteria, survival, and leukemic transition by treatment. Semin Hematol 34, 29-39.

3. IMBERT, M., PIERRE, R., THIELE, J., VARDIMAN, J. W., BRUNNING, R. D., FLANDRIN, G. (2001). Essential thrombocythemia (Lyon: IARC Press).

4. TEFFERI A, THIELE J, ORAZI A, KVASNICKA H M, BARBUI et al. Proposals and rationale for revision of the World Health Organization diagnostic criteria for polycythemia vera, essential thrombocythemia, and primary myelofibrosis. Recommendations from an ad hoc international panel. Blood. 2007; 110:1092-1097.

5. THIELE, J., AND KVASNICKA, H. M. (2003). Chronic myeloproliferative disorders with thrombocythemia: a comparative study of two classification systems (PVSG, WHO) on 839 patients. Ann Hematol 82, 148-152. Epub 2003 February 2022.

6. THIELE, J., KVASNICKA, H. M., FISCHER, R. (1999). Histochemistry and morphometry on bone marrow biopsies in chronic myeloproliferative disorders—aids to diagnosis and classification. Ann Hematol 78, 495-506.

7. THIELE, J., KVASNICKA, H. M., ZANKOVICH, R., DIEHL, V. (2000). Relevance of bone marrow features in the differential diagnosis between essential thrombocythemia and early stage idiopathic myelofibrosis. Haematologica 85, 1126-1134.

8. SCHAFER, A. I. (2004). Thrombocytosis. N Engl J Med 350, 1211-1219.

9. BARBUI, T., BAROSI, G., GROSSI, A., GUGLIOTTA, L., LIBERATO, L. N., MARCHETTI, M., MAZZUCCONI, M. G., RODEGHIERO, F., TURA, S. (2004). Practice guidelines for the therapy of essential thrombocythemia. A statement from the Italian Society of Hematology, the Italian Society of Experimental Hematology and the Italian Group for Bone Marrow Transplantation. Haematologica 89, 215-232.

10. BARBUI, T., FINAZZI, G., DUPUY, E., KILADJIAN, J. J., AND BRIERE, J. (1996). Treatment strategies in essential thrombocythemia. A critical appraisal of various experiences in different centers. Leuk Lymphoma 22 Suppl 1:149-60.

11. CORTELAZZO, S., FINAZZI, G., RUGGERI, M., VESTRI, O., GALLI, M., RODEGHIERO, F., BARBUI, T. (1995). Hydroxyurea for Patients with Essential Thrombocythemia and a High Risk of Thrombosis. N Engl J Med 332, 1132.

12. CORTELAZZO, S., VIERO, P., FINAZZI, G., D'EMILIO, A., RODEGHIERO, F., BARBUI, T. (1990). Incidence and risk factors for thrombotic complications in a historical cohort of 100 patients with essential thrombocythemia. J Clin Oncol 8, 556.

13. HARRISON, C. N. (2002). Current trends in essential thrombocythaemia. British Journal of Haematology 117, 796-808.

14. LENGFELDER, E., HOCHHAUS, A., KRONAWITTER, U., HOCHE, D., QUEISSER, W., JAHN-EDER, M., BURKHARDT, R., REITER, A., ANSARI, H., HEHLMANN, R. (1998). Should a platelet limit of 600×10^9/l be used as a diagnostic criterion in essential thrombocythaemia? An analysis of the natural course including early stages. British Journal of Haematology 100, 15-23.

15. HARRISON, C. N., GALE, R. E., MACHIN, S. J., LINCH, D. C. (1999). A Large Proportion of Patients With a Diagnosis of Essential Thrombocythemia Do Not Have a Clonal Disorder and May Be at Lower Risk of Thrombotic Complications. Blood 93, 417.

16. MILLARD, F. E., HUNTER, C. S., ANDERSON, M., EDELMAN, M. J., KOSTY, M. P., LUIKEN, G. A., MARINO, G. G. (1990). Clinical manifestations of essential thrombocythemia in young adults. Am J Hematol 33, 27-31.

17. JOHNSON, M., GERNSHEIMER, T., JOHANSEN, K. (1995). Essential thrombocytosis: underemphasized cause of large-vessel thrombosis. J Vasc Surg 22, 443-447; discussion 448-449.

18. LAHUERTA-PALACIOS, J. J., BORNSTEIN, R., FERNANDEZ-DEBORA, F. J., GUTIERREZ-RIVAS, E., ORTIZ, M. C., LARREGLA, S., CALANDRE, L., MONTERO-CASTILLO, J. (1988). Controlled and uncontrolled thrombocytosis. Its clinical role in essential thrombocythemia. Cancer 61, 1207-1212.

19. LENGI-BLDER, E., GRIESSHAMMER, M., HEHLMANN, R. (1996). Interferon-alpha in the treatment of essential thrombocythemia. Leuk Lymphoma 22 Suppl 1:135-42.

20. GILLESPIE, E. (1988). Anagrelide: a potent and selective inhibitor of platelet cyclic AMP phosphodiesterase enzyme activity. Biochem Pharmacol 37, 2866-2868.

21. SPENCER, C. M., BROGDEN, R. N. (1994). Anagrelide. A review of its pharmacodynamic and pharmacokinetic properties, and therapeutic potential in the treatment of thrombocythaemia. Drugs 47, 809-822.

22. MAZUR, E., ROSMARIN, A., SOHL, P., NEWTON, J., NARENDRAN, A. (1992). Analysis of the mechanism of anagrelide-induced thrombocytopenia in humans. Blood 79, 1931.

23. TEFFERI, A., SILVERSTEIN, M. N., PETITT, R. M., MESA, R. A., SOLBERG, L. A. J. (1997). Anagrelide as a new platelet-lowering agent in essential thrombocythemia: mechanism of actin, efficacy, toxicity, current indications. Semin Thromb Hemost 23, 379-383.

24. ERUSALIMSKY, J. D., HONG, Y., FRANKLIN, R. (2002). Is the platelet lowering activity of anagrelide mediated by its major metabolite 2-amino-5,6-dichloro-3,4-dihydroquinazoline (RL603)? Exp Hematol 30, 625-626; author reply 626-627.

25. LANE, W. J., HATTORI, K., DIAS, S., PEERSCHKE, E. I., MOORE, M. A., BLANSET, D. L., LANG, P. C., PETRONE, M., RAFII, S. (2001). Anagrelide metabolite induces thrombocytopenia in mice by inhibiting megakaryocyte maturation without inducing platelet aggregation. Exp Hematol 29, 1417-1424.

26. WANG, G., FRANKLIN, R., HONG, Y., ERUSALIMSKY, J. D. (2005). Comparison of the biological activities of anagrelide and its major metabolites in haematopoietic cell cultures. Br J Pharmacol.

27. GAYER R C, DEEB G, PITTMANi K A, SMYTH R D. Disposition of anagrelide, an inhibitor of platelet aggregation. Clin Pharmacol Ther. 1981; 29:381-6

28. McCARTY J M, MELONE P D, SIMANIS J P, KANAMORI D, DESSYPRIS E N, WARSHAMANA, GREENE G S. A preliminary investigation into the action of anagrelide: thrombopoietin-c-Mpl receptor interactions. Exp Hematol. 2006 34:87-96

29. STEURER M, GASTL G, JEDRZEJCZAK W W, PYTLIK R, LIN W, SCHLOGL E et al. Anagrelide for thrombocytosis in myeloproliferative disorders: a prospective study to assess efficacy and adverse event profile. Cancer. 2004; 101:2239-46

30. BIRGEGARD G, BJORKHOLM M, KUTTI J, LARFARS G, LOFVENBERG E, MARKEVAN B et al. Adverse effects and benefits of two years of anagrelide treatment for thrombocythemia in chronic myeloproliferative disorders. Haematologica. 2004; 89:520-7

31. HARRISON C N, CAMPBELL P J, BUCK G, WHEATLEY K, EAST C L, BAREFORD D et al. United Kingdom Medical Research Council Primary Thrombocythemia 1 Study. Hydroxyurea compared with anagrelide in high-risk essential thrombocythemia. N Engl J Med. 2005; 353:33-45

32. BEAVO J A. cGMP inhibition of heart phosphodiesterase: is it clinically relevant? J Clin Invest. 1995; 95:445

33. JAMES C W. Anagrelide-induced cardiomyopathy. Pharmacotherapy. 2000; 20:1224-7

34. ENGEL P J, JOHNSON H, BAUGHAM R P, RICHARDS A I. High-output heart failure associated with anagrelide therapy for essential thrombocytosis. Ann Intern Med. 2005; 143:311-3

35. PACKER M, CARVER J R, RODEHEFFER R J, IVANHOE R J, DiBIANCO R, ZELDIS S M et al. Effect of oral milrinone on mortality in severe chronic heart failure. The PROMISE Study Research Group. N Engl J Med. 1991; 325: 1468-75

36. European Pharmacopea, 6th edition, 2008, Chapter 2.9.3, 267, Apparatus 2

37. Note for Guidance for the Investigation of Bioavailability and Bioequivalence (CPMP/EWP/QWP/1401/98 (July 2001).

The invention claimed is:

1. A pharmaceutical composition free of gastric coating comprising anagrelide HCl having a mean particle size of 5 µm in an amount of between 2 mg and 3 mg, poylacrylacid, and citric acid in an amount of between 15 mg and 19 mg, wherein the amount of the polyacrylacid is between 1.5 and 2.5 fold of the anagrelide (w/w).

2. The pharmaceutical composition according to claim 1, further comprising microcrystalline cellulose.

3. The pharmaceutical composition according to claim 2, wherein the microcrystalline cellulose is present in an amount of between 10 mg and 150 mg.

4. The pharmaceutical composition according to claim 1 having an in-vitro release rate of at least 45% within 8 hours.

5. The pharmaceutical composition according to claim 1, comprising anagrelide HCl, a polyacrylacid, citric acid, microcrystalline cellulose and magnesium stearate.

6. The pharmaceutical composition according to claim 1, wherein the pharmaceutical composition is in the form of a tablet.

7. The pharmaceutical composition according to claim 1, wherein the polyacrylacid is present in an amount of between 3 and 4 mg.

8. The pharmaceutical composition according to claim 3, wherein the microcrystalline cellulose is present in an amount of between 70 mg and 80 mg.

9. A method of treating essential thrombocythemia, comprising administering to a patient in need thereof the pharmaceutical composition of claim 1.

* * * * *